United States Patent
Racz

Patent Number: 5,810,788
Date of Patent: Sep. 22, 1998

[54] R-X NEEDLE

[76] Inventor: Gabor J. Racz, 4412 17th St., Lubbock, Tex.

[21] Appl. No.: 559,436

[22] Filed: Nov. 15, 1995

[51] Int. Cl.$^6$ .................................................. A61M 5/32
[52] U.S. Cl. .......................................... 604/272; 604/264
[58] Field of Search ................................ 604/272, 51–53, 604/44, 273, 274, 264, 117, 158, 164, 165, 166, 170

[56] References Cited

U.S. PATENT DOCUMENTS

| | | |
|---|---|---|
| 3,792,703 | 2/1974 | Moorehead . |
| 4,068,659 | 1/1978 | Moorehead . |
| 4,068,660 | 1/1978 | Beck . |
| 4,141,365 | 2/1979 | Fischell et al. . |
| 4,349,023 | 9/1982 | Gross . |
| 4,379,462 | 4/1983 | Borkan et al. . |
| 4,518,383 | 5/1985 | Evans . |
| 4,529,399 | 7/1985 | Groshong et al. . |
| 4,808,157 | 2/1989 | Coombs . |
| 4,940,458 | 7/1990 | Cohn . |
| 4,958,901 | 9/1990 | Coombs . |
| 5,100,390 | 3/1992 | Lubeck et al. . |
| 5,160,323 | 11/1992 | Andrew . |
| 5,250,035 | 10/1993 | Smith et al. . |
| 5,342,325 | 8/1994 | Lun et al. . |
| 5,360,441 | 11/1994 | Otten . |

OTHER PUBLICATIONS

P.C. Lund; "Principles and Practice of Spinal Anesthesia"; 1971; pp. 262–295.

*Primary Examiner*—John D. Yasko
*Attorney, Agent, or Firm*—Trask, Britt & Rossa

[57] ABSTRACT

An improved needle for use in administering anesthetics, analgesic medications, and the like into the spinal canal through the dura of the spinal cord into the subarachnoid space. The needle comprising a cannula including an improved, unobstructed point thereon and an associated stylet.

15 Claims, 4 Drawing Sheets

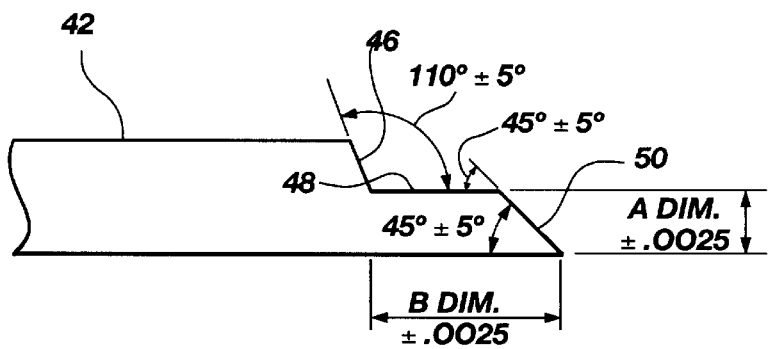
Fig. 4
TABLE I
MEASUREMENTS IN INCHES
| GAGE | A DIM. | B DIM. | CANN. I.D. | CANN. O.D. | STY. WIRE DIA. | CAP COLOR |
|---|---|---|---|---|---|---|
| 17XTW | * See below | 0.110 | .0490-.0510 | .0575-.0590 | .0435-.0440 | Red-Violet |
| 16XTW | * See below | 0.110 | .0545-.0565 | .0645-.0655 | .0520-.0525 | Purple |
| 16TW | * See below | 0.110 | .0525-.0545 | .0645-.0656 | .0400-.0410 | Grey |
| 15TW | * See below | 0.110 | .0595-.0615 | .0715-.0725 | .0520-.0525 | Orange |
* 55% OF CANNULA O.D.
Fig. 5
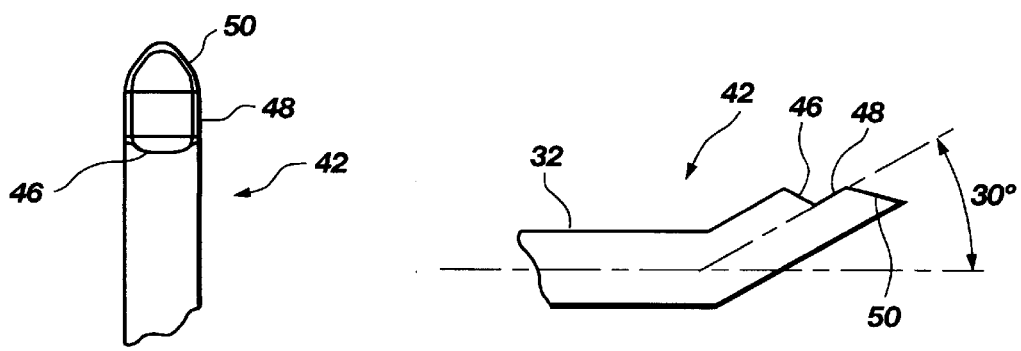
Fig. 6  Fig. 7

TABLE II

MEASUREMENTS IN INCHES

| GAGE | L | CANN. I.D. | W=CANN. O.D. | STY. WIRE DIA. | X=1/2 W |
|---|---|---|---|---|---|
| 17XTW | .1437-.1475 | .0490-.0510 | .0575-.0590 | .0435-.0440 | .0287-.0295 |
| 16XTW | .1612-.1637 | .0545-.0565 | .0645-.0655 | .0520-.0525 | .0322-.0327 |
| 16TW | .1612-.1640 | .0525-.0545 | .0645-.0656 | .0400-.0410 | .0322-.0328 |
| 15TW | .1787-.1812 | .0595-.0615 | .0715-.0725 | .0520-.0525 | .0357-.0362 |

R-X NEEDLE

BACKGROUND OF THE INVENTION

This invention relates to an improved needle for use in administering anesthetics, analgesic medications, and the like into the spinal canal through the dura of the spinal cord into the subarachnoid space.

When administering anesthetics, analgesic medications, and the like into the subarachnoid space of the spinal canal, care must be taken not to traumatize the fibers of the dura and to cause minimal loss of cerebrospinal fluid with each puncture of the dura. It is well established that the loss of cerebrospinal fluid produces extremely severe spinal headaches.

When administering anesthetics into the subarachnoid space by means of spinal needles, it may be necessary to maintain the patient in a horizontal position during the procedure. It may also require the patient to have multiple punctures to the dura to gain access to the subarachnoid space with each puncture increasing the likelihood of the loss of cerebrospinal fluid with the attendant severe spinal headache.

Many spinal needles have a sharp point or chisel-shaped sharp point wherein the fibers of the dura are severed during each puncture procedure. The severing of the fibers of the dura requires a healing period before the wound is fully closed to prevent the escape of cerebrospinal fluid from the spinal canal. Also, catheters inserted through the needle may be cut or severed by the sharp edges of the sharp points or chisel-shaped sharp points on the end of the needles, making it difficult to remove the catheter from the needle or causing the partially severed catheter to traumatize surrounding tissue.

Some spinal needles use a sharp point in combination with a short bevel on the point. However, the use of such a spinal needle may require the needle to be oriented during the insertion procedure to minimize the cutting of the fibers of the dura. Typically, the needle would be inserted with the sharp cutting edges of the bevel being parallel to the longitudinal fibers of the dura. When the dura arachnoid membrane is punctured with such a needle, a distinct dural snap is readily discernable. Such a spinal needle decreases the chance of extradural injection of any local anesthetic but punches a relatively large hole in the dura with the attendant loss of spinal fluid when the needle is withdrawn and the accompanying headache.

Yet other types of spinal needles use a short bevel and an associated orifice on the cannula which is occluded by the stylet in attempt to facilitate unidirectional flow of an anesthetic into the subarachnoid space. However, the bevel on such needles does not have any significant effect on the spread of local anesthetics.

Another type of spinal needle has a sharp point with a completely rounded non-cutting bevel like a pencil point. The tip on such a needle is solid with a distal orifice on one side of the cannula. A fitted stylet, when installed, occludes the distal orifice. The advantage of such a needle is the production of smaller dural puncture holes as the pencil point will separate rather than cut the longitudinal dural fibers. However, such a needle has the disadvantages of resistance to the injection of local anesthetic because the exit hole is smaller than the lumen of the needle, the stylet does not traverse the exit hole making it hard to clear if occluded, the sharp point is easily damaged, and the dural snap during insertion of the needle is absent, making it difficult to feel when inserted.

In another needle, the cannula is beveled, making a smooth junction with the projecting stylet therefrom. Such a needle produces a minimal dural puncture hole. The primary problem of such a needle is that the stylet must be unscrewed from the cannula before being removed, thereby making it time consuming and increasing the possibility of dislodging the needle tip from the subarachnoid space.

Other needles utilize a relatively sharp point and a curved tip to allow the use of plastic tubing or ureteral catheters therethrough. However, the sharp edges of the point cut the plastic tubing. A modified version of this needle uses a bevel which is shorter and blunter, but a sharp stylet protrudes beyond the bevel of the needle which is intended to facilitate the passage of the needle through the various ligamentous structures during insertion to the subarachnoid space.

SUMMARY OF THE INVENTION

The present invention is directed to an improved needle and stylet for use in administering anesthetics, analgesic medications, and the like into the spinal canal through the dura of the spinal cord into the subarachnoid space. The needle comprises a cannula including an improved point to help minimize the cutting of longitudinal fibers of the dura. The improved point further helps to minimize the cutting of any plastic tubing inserted through the needle and allows for the removal of a cut plastic tube with the cannula to help prevent trauma to surrounding tissue. If desired, the improved needle includes a curved point to help direct the insertion of a plastic tube inserted through the needle in the desired direction in the subarachnoid space.

BRIEF DESCRIPTION OF THE DRAWINGS

FIG. 4 is a view of the end of the needle and stylet of the first embodiment of the present invention.

FIG. 5 is Table I setting forth the various dimensions of the needle and stylet of the first embodiment of the present invention shown in drawing FIGS. 3 and 4.

FIG. 6 is a top view of the end of the needle shown in drawing FIG. 4.

FIG. 7 is a side view of the first embodiment of the present invention shown in drawing FIGS. 3 and 4 having a bent end or point.

The present invention will be better understood when the drawings are taken in conjunction with the detailed description of the invention.

DETAILED DESCRIPTION OF THE INVENTION

Figure 1:
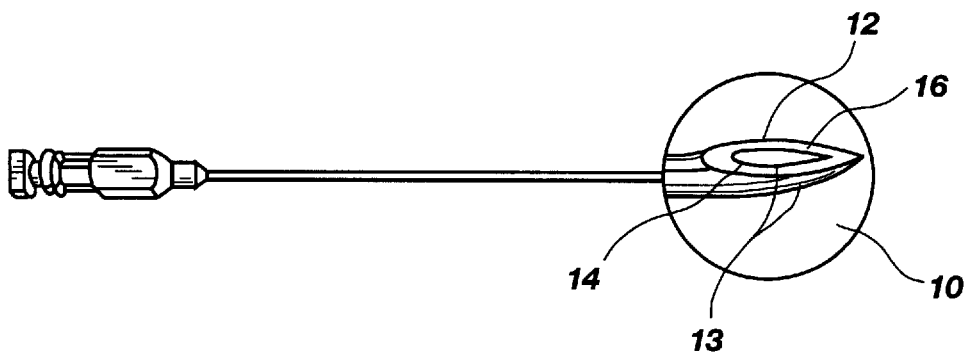
FIG. 1 is a view of a first prior art needle.

Referring to drawing FIG. 1, the point 10 of a prior art Tuohy needle having a Huber point with a medium bevel is shown. The Tuohy needle is shown having a small hub and fitted stylet. The Huber point 10 with a medium bevel is formed or shaped to comprise an opening 12 with cutting edges 13 having a small radius curved portion 14 and a sharply angled or narrow v-shaped portion 16. The point 10 is curved to allow any fluid being ejected therefrom to exit in a known direction. Typically, a slot in the hub indicates the direction of bevel. The sharp inside edge of the bevel increases the hazard of shearing of any plastic tubing or ureteral catheter which is used with the needle, particularly, if it is attempted to withdraw the plastic tubing or catheter without first removing the needle. Even when the edge is blunted, the problem remains. The purpose of the Huber point is to direct the spinal catheter or vinyl tubing in the desired direction and to help prevent impingement of these catheters on various subarachnoid structures and to facilitate the passage of the catheters in the desired direction in the subarachnoid space.

Figure 2:
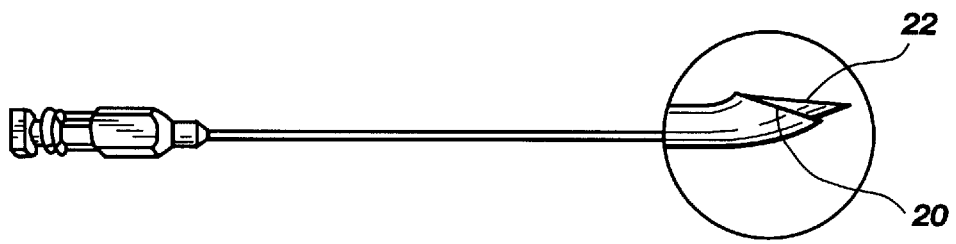
FIG. 2 is a view of a second prior art needle.

Referring to drawing FIG. 2, a modified Tuohy needle is shown. The modified Tuohy needle is commonly known as the Tuohy-Flowers needle. The Tuohy-Flowers needle includes a shorter and blunter bevel 20 than that of the standard Tuohy needle but a sharp stylet 22 protrudes beyond the bevel of the needle which is intended to facilitate the passage of the needle through the various ligamentous structures en route to the subarachnoid space. While the bevel is shorter and blunter than the standard Tuohy needle, the bevel still exhibits the same problem of shearing plastic tubing or catheters inserted therethrough by its sharp edges.

Figure 3:
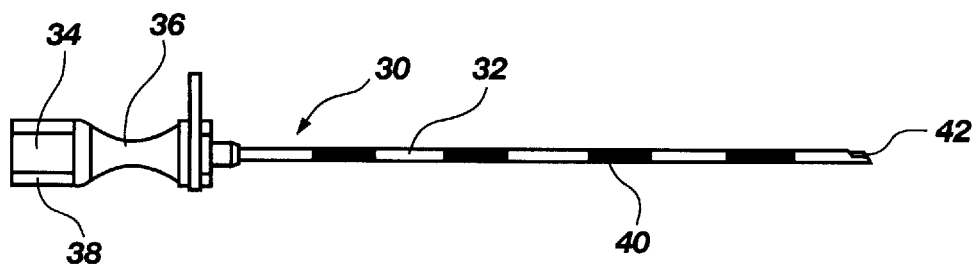
FIG. 3 is side view of a first embodiment of the present invention.

Referring to drawing FIG. 3, the needle 30 of the present invention is shown. The needle 30 comprises a cannula 32 and stylet 34. Both the cannula 32 and stylet 34 include hubs 36 and 38 respectively. The cannula is of any desired length, preferably, 3.500 inches plus or minus 0.125 inches in length. The cannula 32 also includes suitable markings 40 thereon which are spaced a distance of 0.394 inches plus or minus 0.030 inches from the end or point of the cannula and spaced 0.394 inches plus or minus 0.010 inches in between markings to assist in the location of the cannula in use. The cannula is formed having the end shape or point 42 thereon. The stylet is formed having its own end shape or point thereon which differs from that of the cannula. The cannula and stylet can be made of any suitable material.

Referring to drawing FIG. 4 the point 42 of the cannula and stylet is shown in a first embodiment. The point 42 of the cannula or stylet includes a first angled surface 46, horizontal surface 48, and second angled surface 50. The first angled surface 46 is formed at an angle of 110 degrees plus or minus 5 degrees from the horizontal surface 48. The second angled surface 50 is formed at an angle of 45 degrees plus or minus 5 degrees from either the exterior surface of the cannula or the horizontal surface 48.

Referring to drawing FIG. 5, Table I sets forth the various dimensions of the A Dimension (A Dim.) and B Dimension (B Dim.) shown on FIG. 4 as well as their relationship to the cannula internal diameter (Cann. I.D.), cannula external diameter (Cann. O.D.), and the stylet diameter (STY. WIRE DIA.). All the dimensions shown in Table I are in inches. As shown, the various dimensions of Table I relate to various gauge needles where the needles have varying wall thickness; i.e., the gauges being 17, 16 or 15 gauge. As can be seen, each of the various gauge needles set forth in Table I has an A Dimension (A Dim.) of fifty five percent (55%) of the exterior diameter of the cannula (CANNULA O.D.). Also, as shown, each of the various gauge needles set forth in Table I has a B Dimension (B Dim.) of 0.110 inches. Both the A Dimension (A Dim.) and B Dimension (B Dim.) have a tolerance of 0.0025 inches. To eliminate sharp edges on the point 42 of the cannula, all edges and angles of the point 42 are buffed or abrasion blasted to eliminate potential cutting surfaces for cutting any plastic tubing or catheters inserted therethrough. This buffing or abrasion blasting leaves a dull finish on the point of the cannula.

Referring to drawing FIG. 6, the point 42 of the cannula 32 is shown in a top view. As can be seen, the point 42 is formed without any portion thereof being smaller in diameter than the internal diameter of the cannula 32 to prevent the point from shearing or cutting any plastic tubing or catheter inserted therethrough. Also, since the point 42 and all the edges thereof have been buffed or abrasion blasted to remove any sharp cutting edges, the point 42 additionally helps prevent any cutting of any plastic tubing or catheter inserted therethrough.

Referring to drawing FIG. 7, a modified cannula 32 is shown having a bent end or point 42 thereon. The axis of the point 42 may be at any desired angle with respect to the axis of the cannula, such as approximately thirty (30) degrees as shown, to assist in the placement of any plastic tubing or cannula inserted therethrough into the subarachnoid space.

Figures 8, 9:
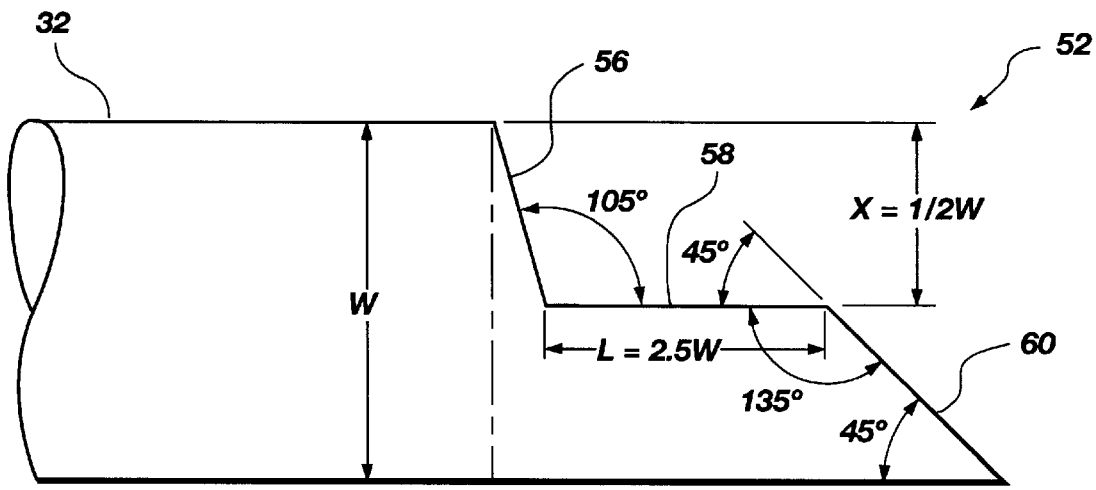
FIG. 8 is a side view of the end of a second embodiment of a needle and stylet of the present invention.
FIG. 9 is Table II setting forth the various dimensions of the needle and stylet of the second embodiment of the present invention shown in drawing FIG. 8.

Referring to drawing FIG. 8, a second embodiment of the present invention is shown. The point 52 of a cannula 32 includes a first angled surface 56, horizontal surface 58, and second angled surface 60. The first angled surface 56 is formed at an angle of 105 degrees with respect to the horizontal surface 58. The horizontal surface 58 is located at a position of one-half of the cannula external diameter. The length of the horizontal surface 58 is two and one-half times the external diameter of the cannula. The second angled surface 60 is formed at an angle of forty five (45) degrees with respect to the exterior surface of the cannula or one hundred and thirty five (135) degrees to the horizontal surface 58, as shown in the previous embodiment of the invention, both angles having a tolerance of plus or minus five (5) degrees.

Referring to drawing FIG. 9, Table II sets forth the various dimensions of the point 52 as shown in FIG. 8 for the various sizes of the cannula as shown and discussed hereinbefore with respect to drawing FIG. 5 and the point 42.

Figure 10:
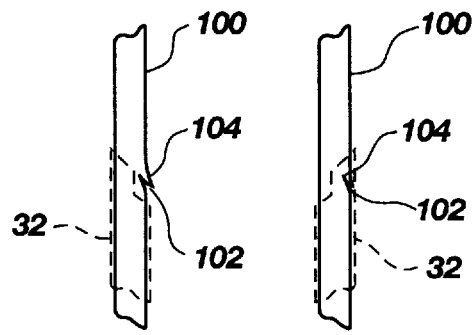
FIG. 10 is a view of the present invention being used with a catheter which has been severed.

Referring to drawing FIG. 10, a portion of plastic tubing or catheter 100 is shown having a cut 102 therein producing a fish hook 104. Also shown (in phantom) is the cannula 32 including a point thereon, either point 42 or 52 described hereinbefore of the present invention, in relation to the plastic tubing or catheter 100. The prior art spinal needles shown in either drawing FIG. 1 or 2 prevent the cut plastic tubing or catheter from being pulled back through the needle because the fish hook 104 on the plastic tubing or catheter 100 is caught on the smaller portion 16 of the bevel or point 10. The sharp edges of the bevel 10 also may cut the plastic tubing or catheter during use. With the present invention, since the shape of the point 42 or 52 does not obstruct the bore of the cannula, the plastic tubing or catheter 100 may be removed by pulling it through the bore of the cannula by first rotating the cannula until the cut 102 and fish hook 104 of the plastic tubing or catheter is covered by a portion of the point 42 or 52 as shown on the right side view of drawing FIG. 10. In this manner the cut is covered by a portion of the point 42 or 52 as well as the fish hook 104 being retained within the cannula 32, thereby facilitating the removal of the plastic tubing or catheter 100. This also protects any surrounding tissue from being traumatized by the fish hook 104 on the plastic tubing or catheter 100. In contrast, the prior art needle shown in drawing FIGS. 1 and 2 only allows the withdrawal of the cannula and the plastic tubing or catheter together as the fish hook 104 on the plastic tubing or catheter 100 will hang in the point 10 and any surrounding tissue may be traumatized by the fish hook 104.

Figure 11:
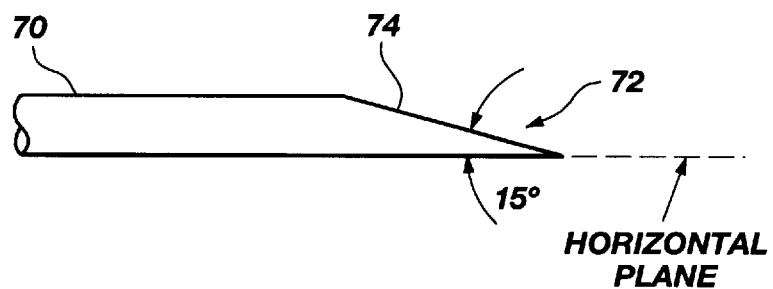
FIG. 11 is a view of the point of the stylet used in the cannula of the needle of the present invention.

Referring to drawing FIG. 11, the point of the stylet 34 used in the present invention is shown. The stylet body 70 is formed having a point 72 which includes an angled surface 74 formed at an angle of fifteen (15) degrees with respect to the exterior diameter of the body 70. The angle has a tolerance of plus or minus five (5) degrees. In this manner the point 72 of the stylet 34 includes a relatively long flat surface thereon which does not interfere with the point 42 on the cannula 32 of the needle 30 during insertion thereof.

It should be recognized and understood that the needle of the present invention offers significant advantages over prior art needles. The needle of the present invention includes a cannula having a point having, in turn, an unobstructed bore therethrough. The point of the cannula has no sharp edges to minimize any trauma to tissue and/or cutting of any tubing or catheter inserted therethrough. The point of the cannula easily separates with minimal trauma the longitudinal fibers of the dura and yields a distinct dural snap upon insertion. The point of the cannula allows easy insertion of tubing or a catheter therethrough with its subsequent direction into the subarachnoid space. The cannula further allows the ready removal of any cut tubing or catheter with minimal trauma to surrounding tissue.

Having described the invention it will be obvious that changes, additions, deletions, and substitutions may be made which fall within the scope of the claimed invention.

What is claimed is:

1. A needle for insertion in the subarachnoid space of the human body and the like, said needle comprising:

a cannula having a bore therethrough and a hub thereon;

a stylet having an exterior diameter smaller than the bore of the cannula to allow passage therethrough; and a point on the cannula having substantially the same diameter as the bore of the cannula a first angled surface, a horizontal surface extending from the first angled surface, and a second angled surface extending from one end of the horizontal surface.

2. The needle of claim 1 wherein the first angled surface extends upwardly at an angle of approximately 110 degrees from the horizontal surface and the second angled surface extends downwardly at an angle of approximately 45 degrees from the horizontal surface.

3. The needle of claim 1 wherein the cannula includes a plurality of markings thereon at a known predetermined distance from the point of the cannula.

4. The needle of claim 1 wherein the horizontal surface of the point of the cannula is located at substantially 55 percent of the exterior diameter of the cannula.

5. The needle of claim 1 wherein the horizontal surface has a length of substantially 0.110 inches.

6. The needle of claim 1 wherein the point of the cannula is formed at an angle with respect to the cannula.

7. The needle of claim 1 wherein the first angled surface extends substantially upwardly at an angle of substantially 105 degrees from the horizontal surface and the second angled surface extends downwardly at an angle from the horizontal surface of substantially 45 degrees therefrom.

8. The needle of claim 7 wherein the horizontal surface has a length of substantially 2.5 times the exterior diameter of the cannula.

9. The needle of claim 1 wherein the stylet includes a point thereon.

10. The needle of claim 9 wherein the stylet includes a point thereon formed at substantially a 15 degree angle with respect to a horizontal plane at the bottom of the stylet.

11. The needle of claim 1 wherein the cannula has a length of substantially 3.5 inches from the point to the hub.

12. The needle of claim 1 wherein the bore of the cannula is substantially unobstructed by any portion of the point of the cannula.

13. The needle of claim 1 wherein the point on the cannula includes substantially no sharp edges.

14. The needle of claim 13 wherein the point of the cannula is burnished to substantially eliminated sharp edges.

15. The needle of claim 7 wherein the horizontal surface is located at a position in the point of substantially one-half the external diameter of the cannula.

* * * * *